US00PP21761P3

(12) United States Plant Patent
Patel

(10) Patent No.: US PP21,761 P3
(45) Date of Patent: Mar. 8, 2011

(54) BLUEBERRY VARIETY NAMED 'SUNSET BLUE'

(50) Latin Name: *Vaccinium corymbosum*
Varietal Denomination: Sunset Blue

(75) Inventor: Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/590,285

(22) Filed: Nov. 5, 2009

(65) Prior Publication Data

US 2010/0115677 P1 May 6, 2010

Related U.S. Application Data

(60) Provisional application No. 61/198,481, filed on Nov. 6, 2008.

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Greenlee Sullivan PC

(57) ABSTRACT

A new and distinct Northern Highbush blueberry variety is described. The variety results from selection among a population of seedlings derived from crossing the blueberry variety known as 'Reka' (U.S. Plant Pat. No. 6,700) and an unreleased seedling selection called B7.8.1 (not patented). The fruit of this new variety is medium to large, with strong bloom, good flavor with a good balance between sugar and acidity, and extended shelf life. Plant is upright with good vigor and an early heavy crop. The new variety has been named 'Sunset Blue'.

10 Drawing Sheets

Genus and species of plant named: *Vaccinium corymbosum.*

Variety denomination: Sunset Blue.

BACKGROUND OF THE INVENTION

This new Northern Highbush blueberry variety was selected from a population of seedlings derived from crossing the blueberry varieties known as 'Reka' (U.S. Plant Pat. No. 6,700) and an unnamed seedling selection called B7.8.1 (not patented). The cross was made in 1988 and the new variety was selected in 1996 from among plants located at Ruakura, Hamilton, New Zealand, and was assigned the breeder code, RH11. The new variety has since been named 'Sunset Blue'.

SUMMARY OF THE INVENTION

The fruit of this new variety is medium to large, with strong bloom, good flavour with a good balance between sugar and acidity, and extended shelf life. Plant is upright with good vigour and an early heavy crop. The new variety was originally referred to as 'RH11' but has since been named 'Sunset Blue'.

The new variety is characterised as follows:

Maturity period: Early season, from the end of November to mid December at the Ruakura, Hamilton, New Zealand, about a week earlier to that of 'Reka' and 'Nui' and a week later than 'Marimba' and 'Misty'.

Plant form and vigour: The plant is upright in habit, with good vigour, similar to 'Reka'.

Yield: Heavy crop early in the summer.

Berry size: Medium to big fruit.

Color: Medium blue, sometime showing red on the back (stem end) of fruit.

Fruit bloom: Strong intensity; attractive.

Pedicel scar: Small to medium dry scar similar to 'Reka' and 'O'Neal'.

Plant health: Little incidence of anthracnose (*Colletotrichum acutatum*) on fruit has been observed.

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

FIG. 3 shows typical adult plants of 'Sunset Blue' planted in the field.

DETAILED DESCRIPTION

Figure 1:
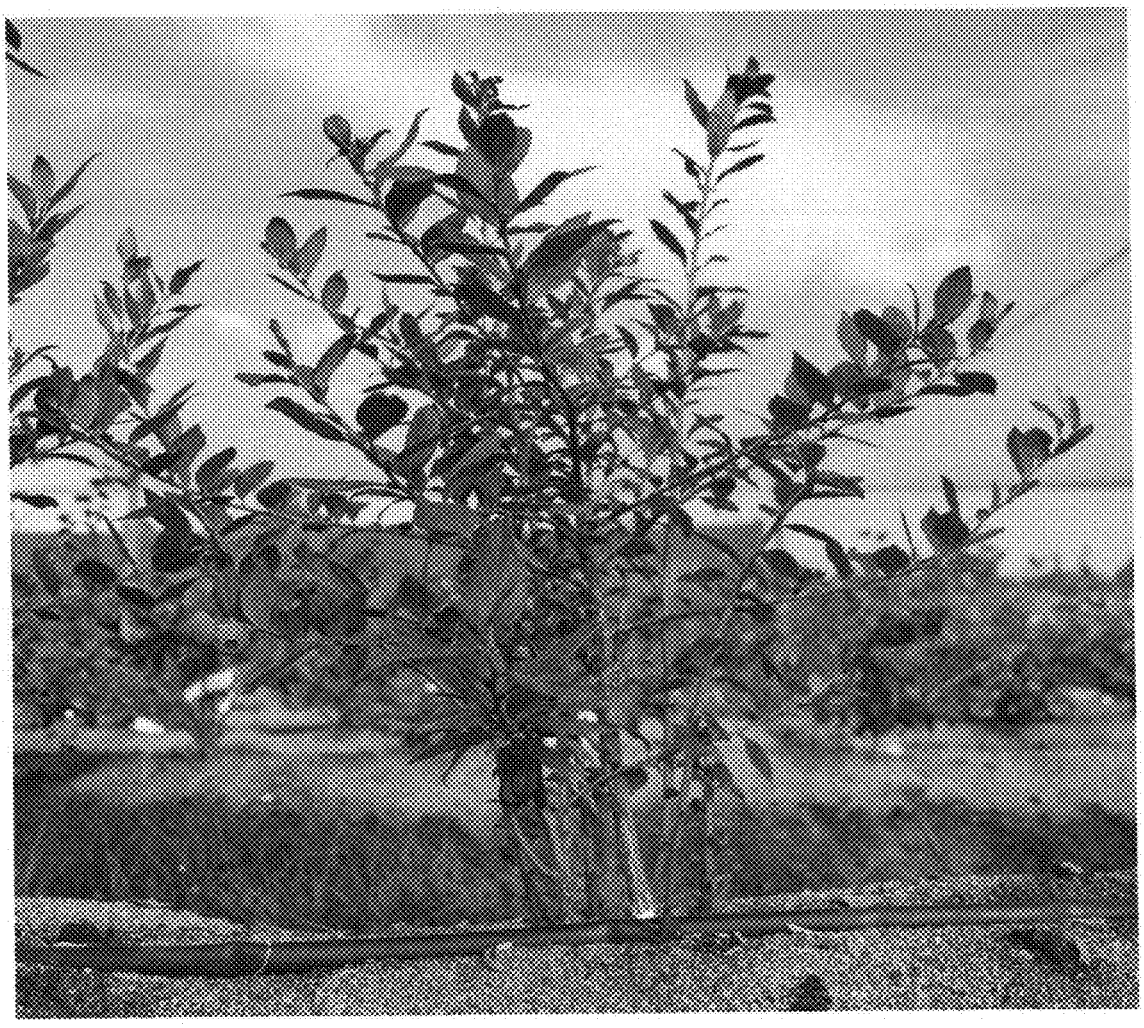
FIG. 1 shows a young plant of 'Sunset Blue' taken in April 2008.
Figure 2A:
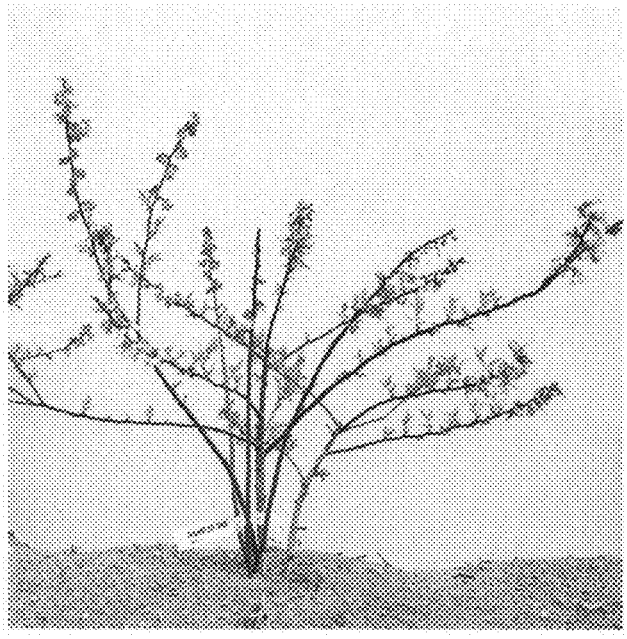
FIG. 2A shows a young plant of 'Sunset Blue' during flowering taken in September 2008.
Figure 2B:
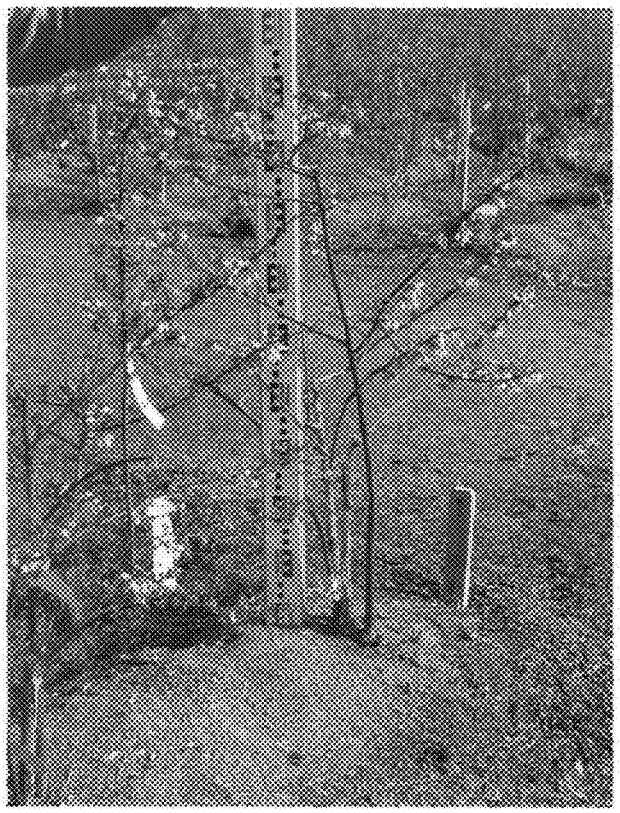
FIG. 2B shows a young plant of 'Sunset Blue' during flowering taken in September 2009.
Figure 3A:
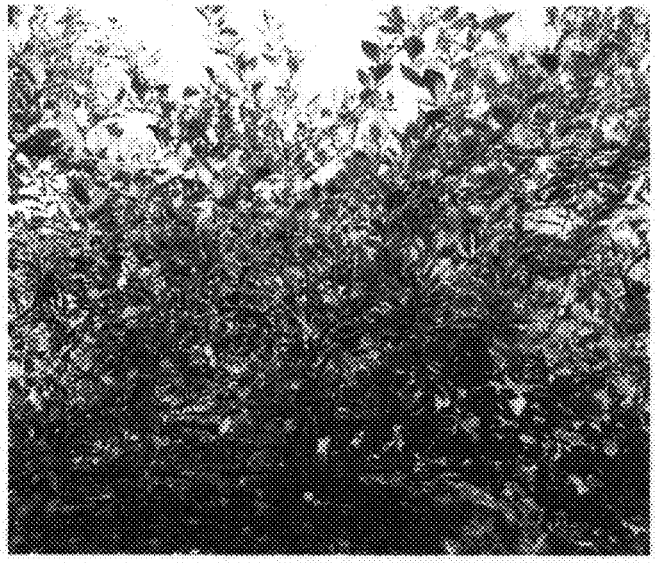
FIG. 3A shows the adult plant at the end of the summer (March 2008)
Figure 3B:
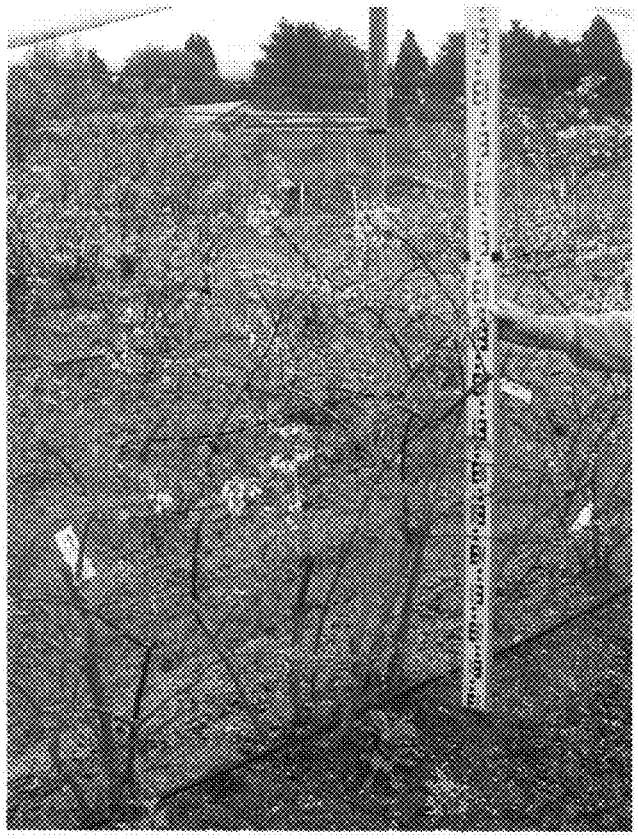
FIG. 3B shows the plant during flowering time the following year (September 2009).
Figure 4:
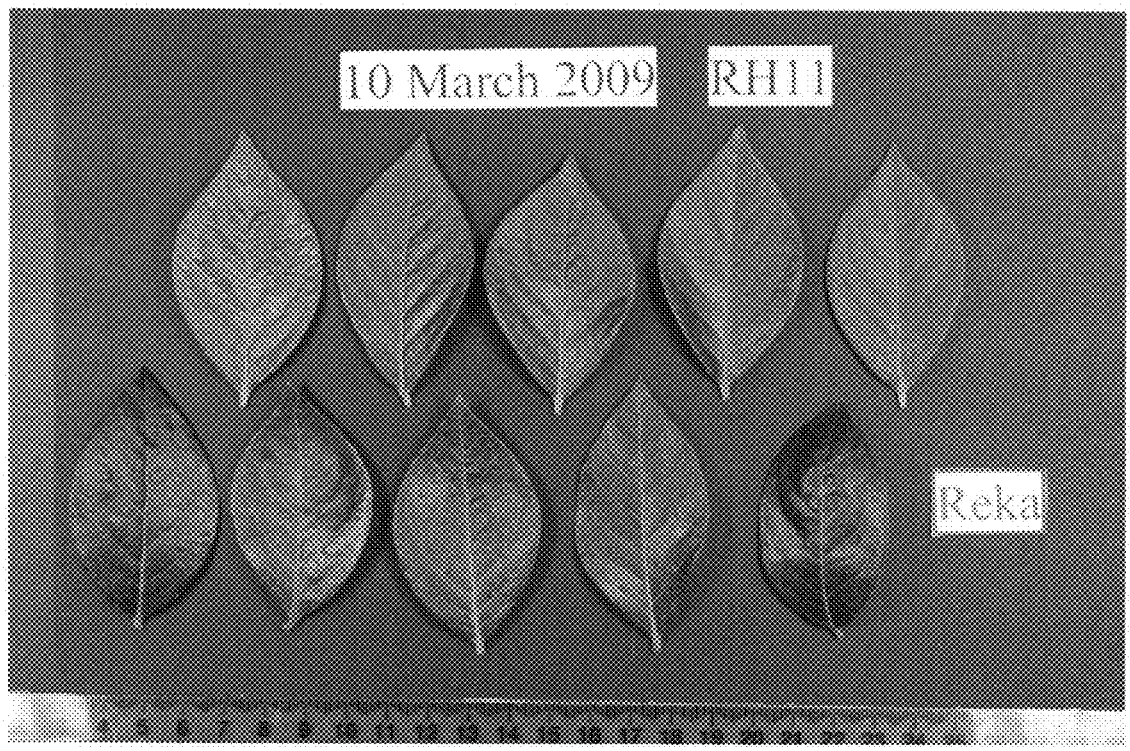
FIG. 4 shows the characteristic leafing of 'Sunset Blue' (labeled in the figure as 'RH11').
Figure 5:
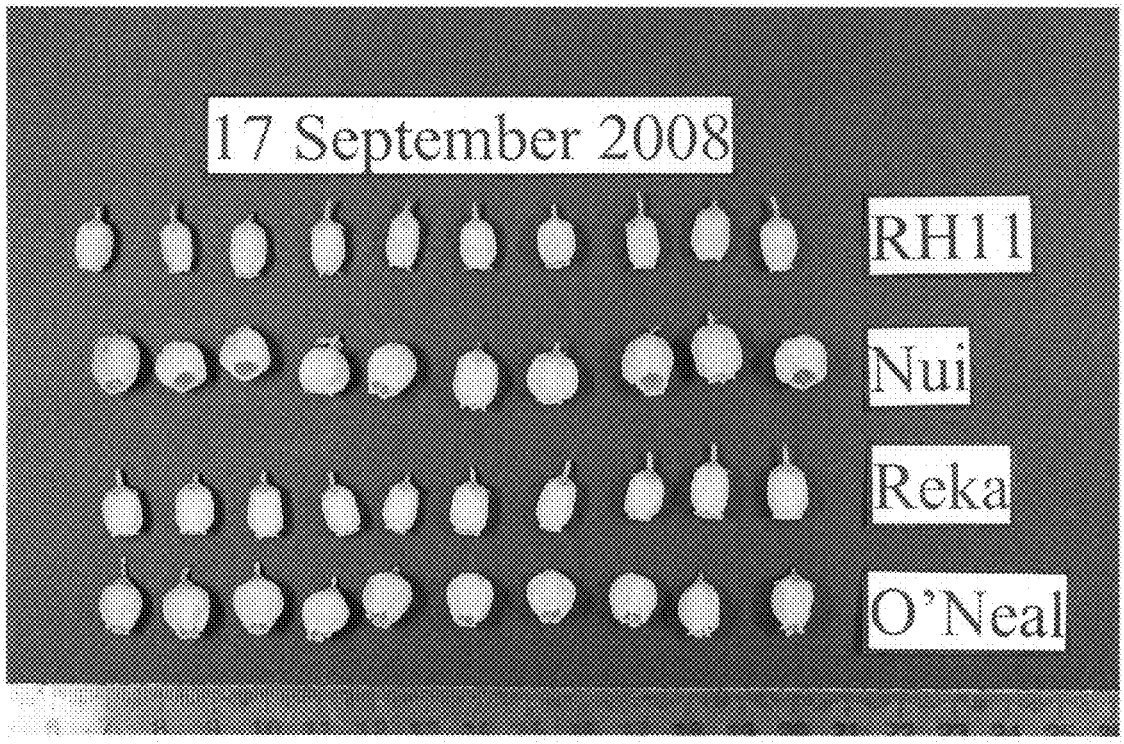
FIG. 5 shows the characteristic flowers of 'Sunset Blue' (labeled in the figure as 'RH11') compared to flowers of commercial varieties (September 2008).
Figure 6:
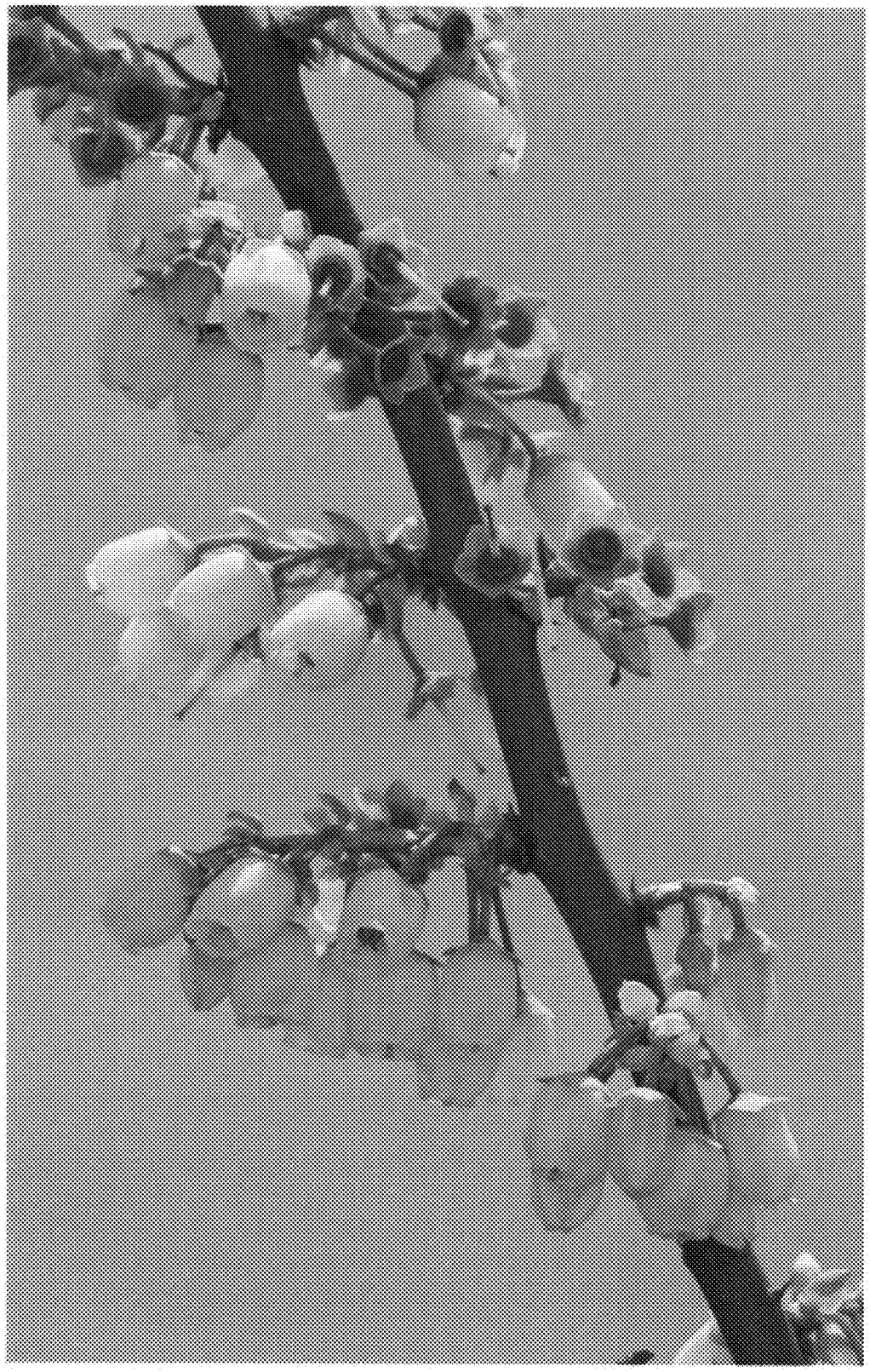
FIG. 6 shows a close up of the characteristic flowers coloration of 'Sunset Blue'.
Figure 7:
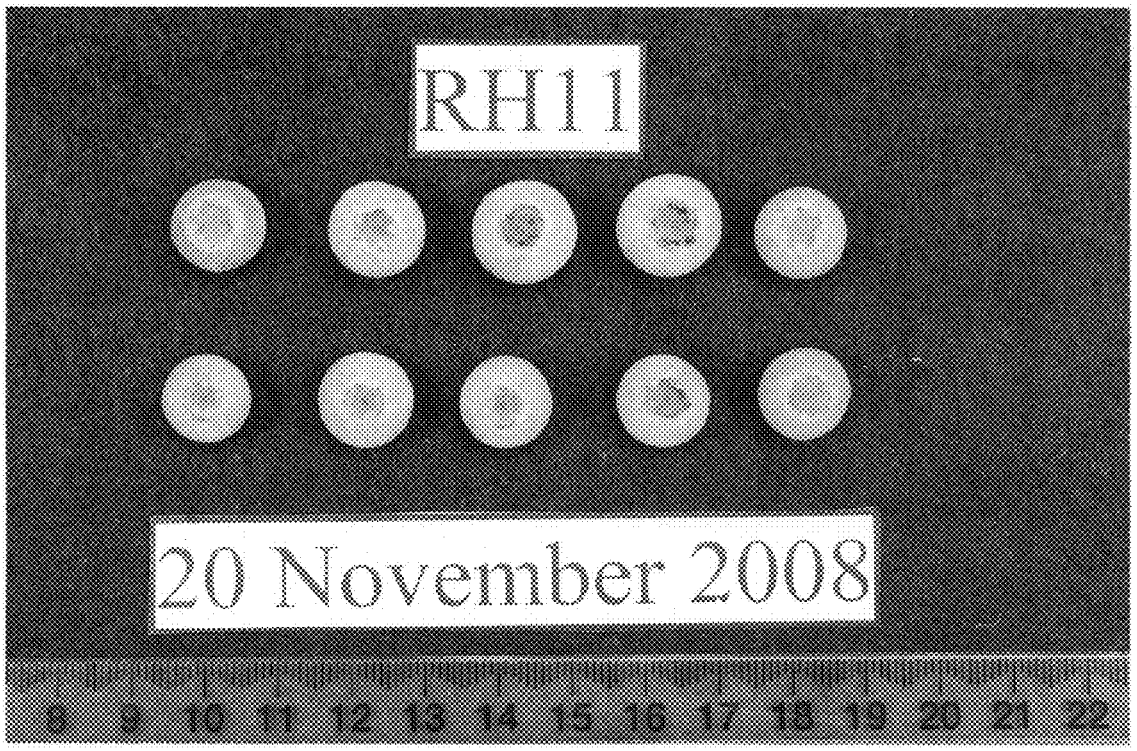
FIG. 7 shows green fruit of 'Sunset Blue' (labeled in the figure as 'RH11').
Figure 8:
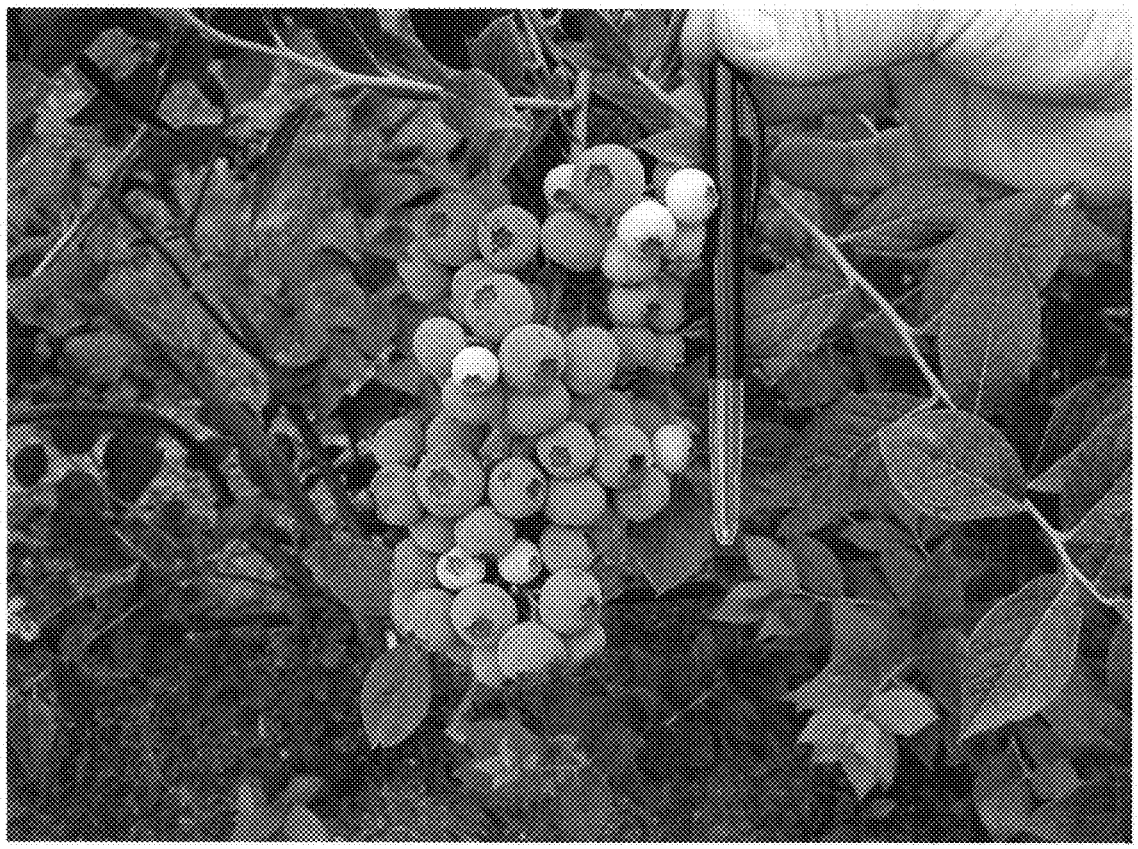
FIG. 8 shows the characteristic fruit of 'Sunset Blue'.
Figure 9A:
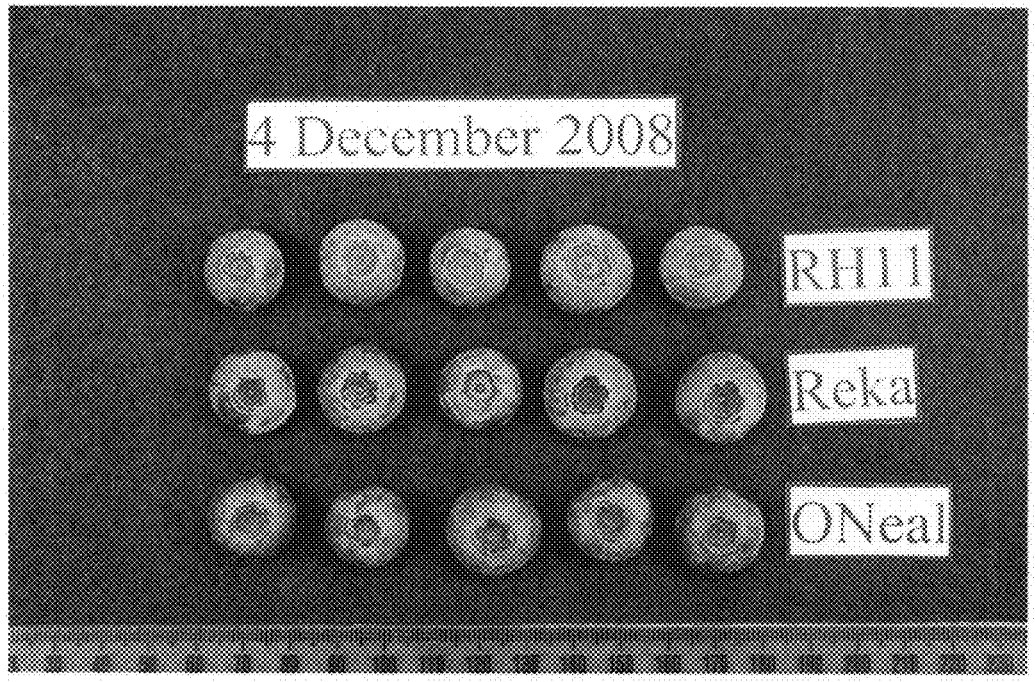
FIGS. 9A and 9B show the characteristic fruit of 'Sunset Blue' (labeled in the figures as 'RH11') compared to other varieties. Fruit is showed from the calyx (FIG. 9A) and from the pedicel scar (FIG. 9B).
Figure 9B:
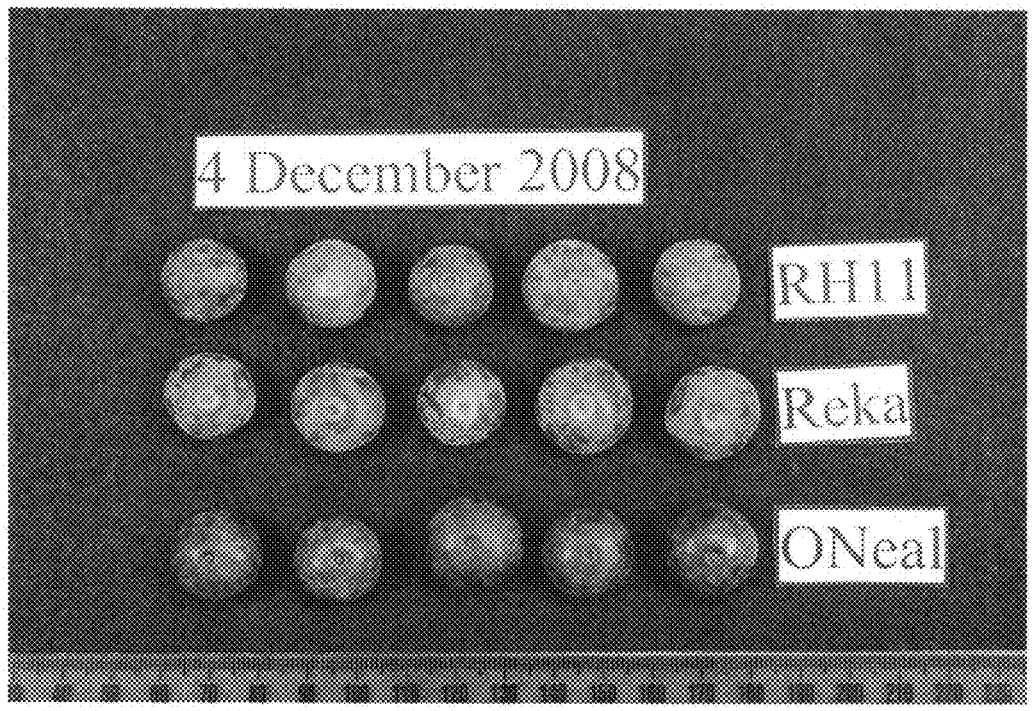
Figure 10:
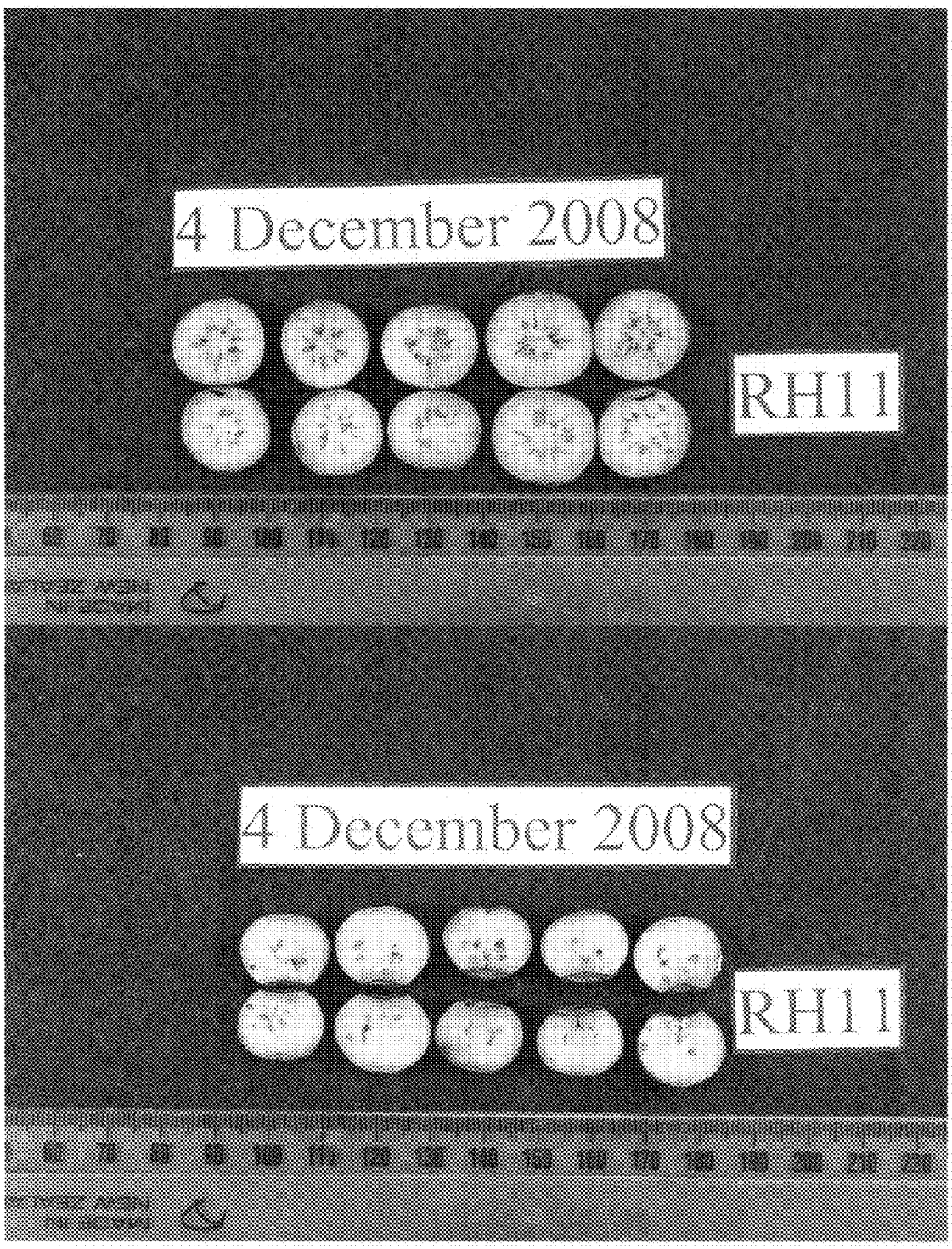
FIG. 10 shows the fruit sections of 'Sunset Blue' (labeled in the figure as 'RH11').

The observations, unless otherwise specified, were made in the 2008 and 2009 seasons on nine year old plants propagated and grown at Ruakura, Hamilton, New Zealand and additional information was collected from young plants (3-5 years old). All dimensions in millimeters, weights in grams (unless otherwise stated). Color terminology is in accordance with The Royal Horticultural Society Colour Charts 2001 edition.

Plant and foliage

This tetraploid plant is upright, with good vigour, similar to 'Reka'.

The mature leaf is ovate in shape and typically averages 62 mm in length and approximately 31 mm in width, similar to the leaf size of plants of the variety 'Reka' (U.S. Plant Pat. No. 6,700) (63 mm in length and 36 mm in width) and smaller than those of 'Duke' (70 mm in length, 42 mm in width) and 'Nui' (80 mm in length, 50 mm in width). Generally the leaf margin has no serration, medium glossiness on the upper surface similar to 'Reka', and no glaucescence on the upper surface. Typically the petiole length averages 3.9 mm.

The color of the leaf is near Green 137A, differing from those of the varieties 'Nui' (near Green 146A) and 'Reka' (near Green 139A). The leaf vein color is near Yellow-Green 145A, differing from those of the variety 'Nui' (near Yellow-Green 152C).

The color of mature dormant wood is near Greyed-Purple 185B on the top side of the cane and Greyed-Purple 183D on the underside of the same cane, differing from that of the variety 'Nui' (near Greyed-Red 181A and B on the top side of the cane and Yellow-Green 146C on the underside of the same cane).

Inflorescence

The average number of flower buds per shoot is 9, with an observed range of 3-12. The estimation of number of buds per shoot was made on the fruiting (terminal) sections of shoots; this section typically averaging 10 cm in length and the average total shoot length is 30 cm.

Flowers are generally clustered and the width of the typical flower averages 6.7 mm, smaller than 'Reka' (averaging 7.7 mm) and 'Nui' (10.3 mm). The background color of the petals on fully open mature flowers is near White 155C occasionally with a little anthocyanin coloration near Red 55A and 55D.

Fruit

The fruit are medium to large under New Zealand growing conditions, averaging approximately 2.1 g. Observations indicate fruit size to be similar to that of the parent 'Reka' and smaller than that of fruit of the variety 'Nui' (3.2 g).

Generally, fruit is oblate in shape. Fruit diameter averages approximately 16.3 mm (observed range 14.7-17.5 mm) under New Zealand growing conditions. Unripe fruit is green, within the range near Yellow-Green 145B. Ripe fruit has an attractive bloom. Fruit color is medium blue, with the bloom intact, near Blue 103C, sometime showing reddish coloration around the pedicel scar, similar to 'Reka'. Skin color when bloom is completely removed is near Black 202A, again sometimes showing reddish coloration around the pedicel scar.

The pedicel scar is small to medium, approximately 1.8 mm in diameter, similar to 'Reka'. The scar is generally dry. The fruit sweetness is medium and the Brix level averages 11.4%, (observed range 9-13%), similar to 'Reka' and 'Nui' (12% and 11.8% respectively).

The fruit acidity measured as titratable acidity (%) averaged 0.65, similar to 'Reka' and less than 'Nui' (0.8%). Fruit is generally of medium to high firmness, averaging 190 g/mm (observed range 170-210 g/mm), firmer compared with fruit of the varieties 'Reka' (averaged 168 g/mm) and 'Nui' (averaged 150 g/mm). Yield is high, averaging over 4 Kg per adult plant under New Zealand growing conditions, superior to 'Reka' and 'Nui'.

Events

According to observations the time of vegetative bud burst was around the end of August, similar to 'Marimba', about 5 days earlier than 'Nui' and 12-14 days earlier than 'Reka'. The new variety reaches an estimated 50% of the flowering around the 26 September, similar to 'Nui' and 'Reka'.

The fruit maturity period occurs early in the season; typically the fruit commenced ripening around the end of November to mid December at the Ruakura, Hamilton, New Zealand, In 2008 50% of ripe fruit on the bush was estimated to occur 1 December, about one week earlier than 'Reka' and two weeks earlier than 'Nui'. According to observations on flowering and fruit ripening, 'Sunset Blue' completes its fruit development between one and two weeks earlier than the varieties 'Reka' and 'Nui'.

Disease and pests

The plant showed symptoms of the early stage of anthracnose fruit rot (*Colletotrichum acutatum*) on fruit during the summer 2007 which was atypically wet during the fruit ripening period.

The invention claimed is:

1. A new and distinct Northern Highbush blueberry variety substantially as described in the specification and illustrations.

* * * * *